United States Patent
LeBlanc

(10) Patent No.: US 7,784,946 B2
(45) Date of Patent: Aug. 31, 2010

(54) VIRTUAL MICROSCOPE SYSTEM FOR MONITORING THE PROGRESS OF CORNEAL ABLATIVE SURGERY AND ASSOCIATED METHODS

(75) Inventor: Richard Alan LeBlanc, Clermont, FL (US)

(73) Assignee: Alcon Refractivehorizons, Inc., Fort Worth, TX (US)

( * ) Notice: Subject to any disclaimer, the term of this patent is extended or adjusted under 35 U.S.C. 154(b) by 0 days.

(21) Appl. No.: 12/337,705

(22) Filed: Dec. 18, 2008

(65) Prior Publication Data

US 2010/0157244 A1      Jun. 24, 2010

Related U.S. Application Data

(60) Provisional application No. 61/015,853, filed on Dec. 21, 2007.

(51) Int. Cl.
*A61B 3/14* (2006.01)
(52) U.S. Cl. .................. 351/210; 351/221; 351/246
(58) Field of Classification Search .......... 351/205, 351/206, 210, 212, 221, 246, 247
See application file for complete search history.

(56) References Cited

U.S. PATENT DOCUMENTS 4,786,154 A    11/1988  Fantone et al.
5,067,804 A    11/1991  Kitajima et al.
2007/0121203 A1  5/2007  Riederer
2008/0058734 A1*  3/2008  Hanft et al. ................. 604/289

FOREIGN PATENT DOCUMENTS

WO      0030528 A    6/2000
WO   2006000072 A    1/2006

\* cited by examiner

*Primary Examiner*—Huy K Mai
(74) *Attorney, Agent, or Firm*—Armando Pastrana, Jr.

(57) ABSTRACT

A system for visualizing an eye of a patient during corneal surgery includes a processor and a first and second camera in signal communication with the processor. The cameras are positionable for focusing on a cornea positioned for surgery. A first and a second display and optics therefor are in signal communication with the processor and are positionable for viewing through a first and a second eyepiece of a stereo microscope, respectively. Software is resident on the processor for receiving a first and second corneal image from the first and second cameras, for processing the received first and second images for display, and for transmitting the processed first and second images to the first and the second displays, respectively, via the display optics. The displays can then be viewed by a surgeon through the microscope at least during the surgery.

11 Claims, 5 Drawing Sheets

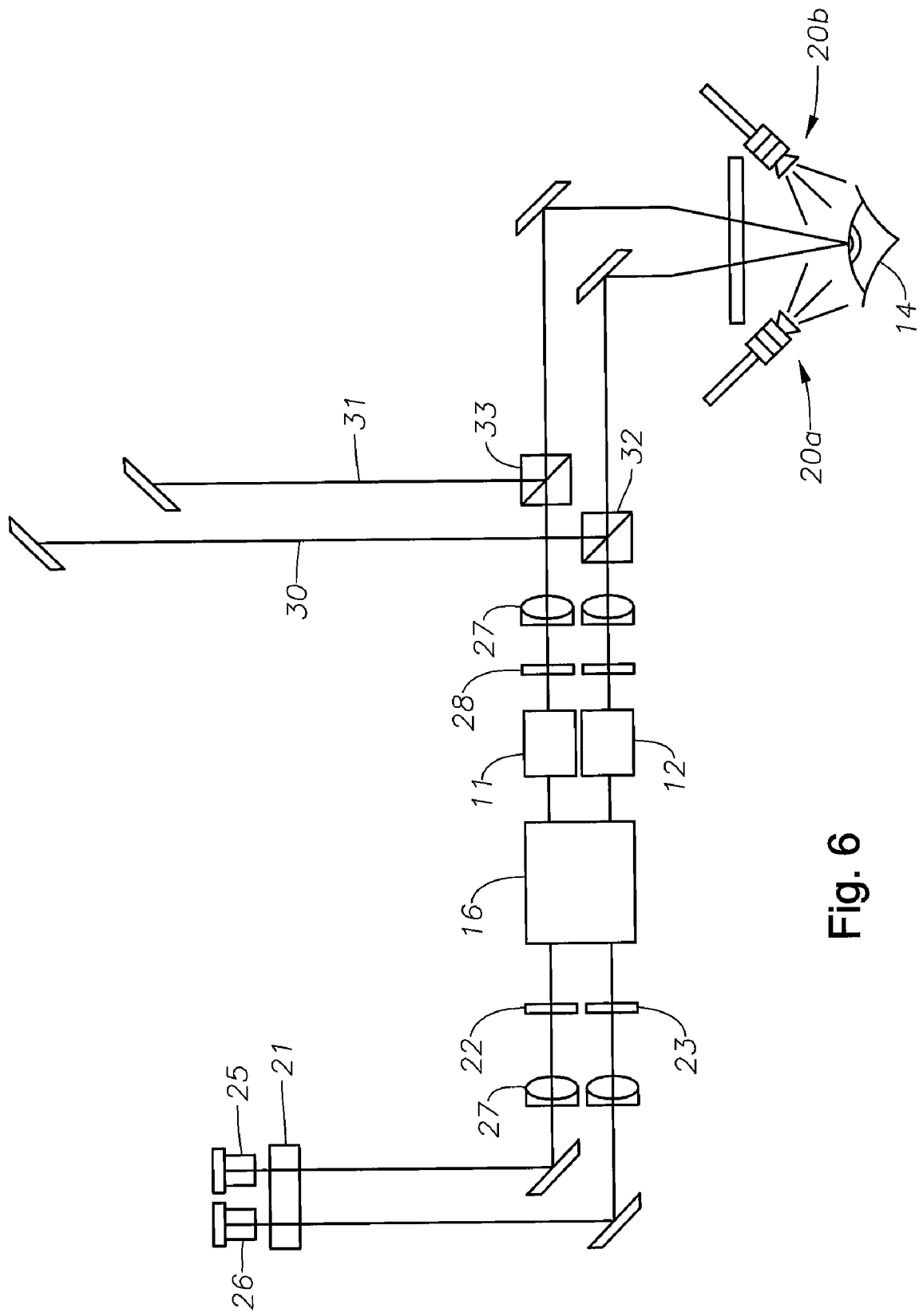

VIRTUAL MICROSCOPE SYSTEM FOR MONITORING THE PROGRESS OF CORNEAL ABLATIVE SURGERY AND ASSOCIATED METHODS

This Application Claims the Priority of U.S. Provisional Application No. 61/015,853 Filed Dec. 21, 2007.

FIELD OF THE INVENTION

The present invention generally relates to surgical methods and, in particular, to systems and methods for monitoring the progress of corneal ablative surgery.

BACKGROUND

The performance of LASIK (laser in situ keratomileusis) surgery is typically accompanied by the cutting of a thin flap in the cornea, which is then lifted and folded back along a hinge to expose the corneal stroma beneath. An ablating laser is used to perform refractive surgery, and the flap is replaced.

Several methods have been used to avoid or detect any "wrinkles," or striae, in the corneal flap after replacement atop the stroma. For example, the cornea can be marked prior to cutting so that the markings can be used to realign the flap. Another method employs the operating (direct-view) microscope and a diffuse, broadband, white light source to detect striae. Alternatively, the refractive surgeon may use a dedicated apparatus, such as a handheld slit lamp, to project a thin line of visible broadband, white light onto the cornea to scan for surface aberrations or edges.

However, the flooding of the eye with such illumination to detect flap position, debris, and hydration can be uncomfortable for the patient, and the use of a slit lamp to detect flap replacement and general eye condition can compromise work flow. Further, white light may not provide optimal enhancement of parts of the eye for visualization. To view at alternate wavelengths, external camera systems with standard video monitors can be used, but, in order to eliminate the high illuminations required for direct-view microscopes, larger apertures must be used, mandating a tradeoff between patient safety and doctor view.

SUMMARY OF THE INVENTION

The present invention is directed to a system and method for visualizing an eye of a patient during corneal surgery. The system comprises a processor and a first and a second camera in signal communication with the processor. The first and the second cameras are positionable for focusing on a cornea of the eye that is positioned for undergoing surgery.

A first and a second display and optics therefor are in signal communication with the processor and are positionable for viewing through a first and a second eyepiece of a stereo microscope, respectively. The microscope is associated with a surgical field of the cornea.

Software is resident on the processor that comprises code segments for receiving a first and a second image of the cornea from the first and the second cameras, and for processing the received first and second images for display. A code segment is also provided for transmitting the processed first and second image to the first and the second displays, respectively, via the display optics. The first and the second displays can then be viewed by a surgeon through the microscope at least during the surgery, and, preferably, before and after the surgery as well.

The invention is also directed to a method for monitoring a process of corneal surgery. The method comprises the steps of illuminating an eye comprising a cornea positioned for undergoing surgery and stereoscopically imaging the cornea onto a first and a second display. The first and the second display can be viewed through a first and a second eyepiece of a stereo microscope, respectively.

The features that characterize the invention, both as to organization and method of operation, together with further objects and advantages thereof, will be better understood from the following description used in conjunction with the accompanying drawing. It is to be expressly understood that the drawing is for the purpose of illustration and description and is not intended as a definition of the limits of the invention. These and other objects attained, and advantages offered, by the present invention will become more fully apparent as the description that now follows is read in conjunction with the accompanying drawing.

BRIEF DESCRIPTION OF THE DRAWING

FIG. 6 is a schematic of the eye imaging and display system of the present invention incorporated into a LASIK apparatus.

DETAILED DESCRIPTION OF THE PREFERRED EMBODIMENT

A description of the preferred embodiments of the present invention will now be presented with reference to FIGS. 1-7.

Figure 1:
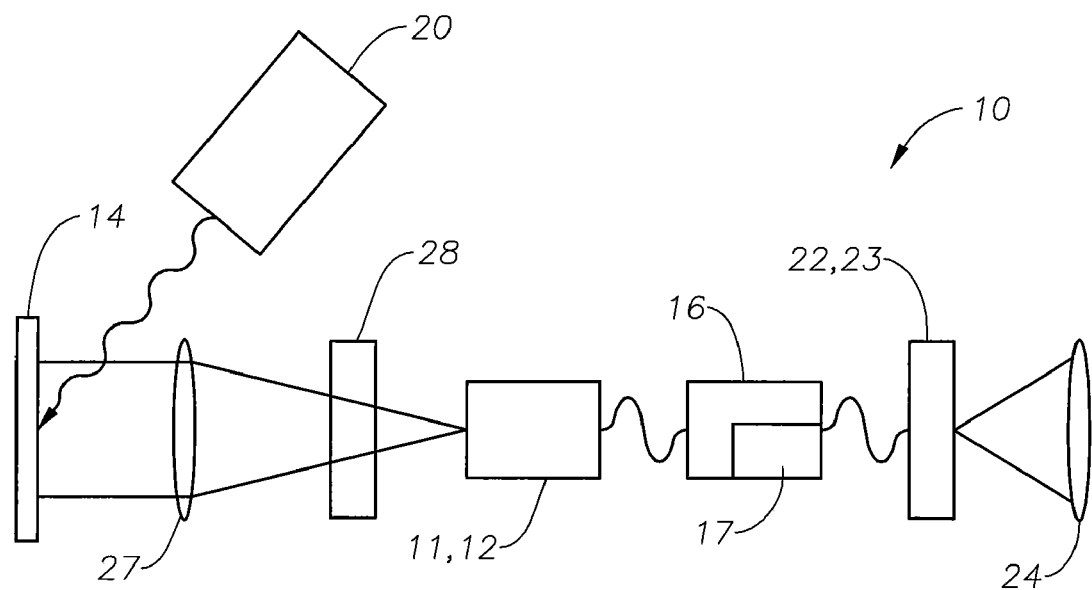
FIG. 1 is a schematic of the eye imaging and display system of the present invention.
Figure 2:
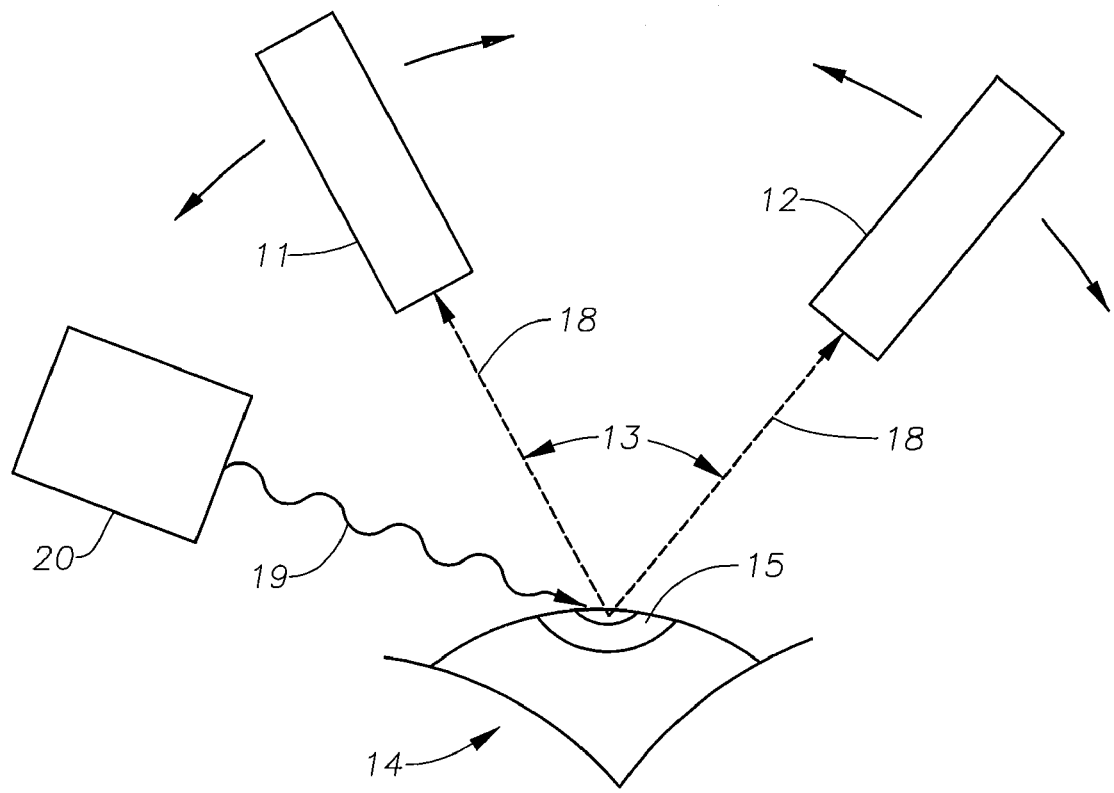
FIG. 2 is a schematic of the cameras imaging an eye.

The system schematic of FIG. 1 illustrates the elements of an exemplary embodiment of a system 10 of the present invention for monitoring a process of corneal surgery by a surgeon. The system 10 comprises a first 11 and second 12 high-resolution color camera (FIG. 2) that in a particular embodiment are adjustable in angular separation 13 and can focus on a portion of an eye 14, for example, the cornea 15. An exemplary surgical procedure for which the system 10 is applicable is LASIK surgery, although this is not intended as a limitation, and is also applicable to pupilometry, where pupil dynamics can be monitored and recorded, and other eye measurements, such as corneal birefringence, and to other ophthalmic surgeries, where a surgical microscope might be useful. For this type of surgery, the system 10 can be useful for imaging the cornea 15, a flap cut in the cornea, the underlying stroma, the limbus, and any other portion of the eye desired to be imaged, and can provide depth perception.

The cameras 11, 12 can be optimized for low light levels, wide band, or speed. Preferably, the speed is sufficient so as not to show a noticeable lag in imaging. The waveband should preferably encompass the wavelengths expected to be used for image enhancement, and the sensitivity should allow comfortable light levels on the patient.

The cameras 11, 12 are in signal communication with a processor 16 that has image processing software 17 resident thereon. The cameras 11, 12 are positioned and focused for receiving reflected radiation 18 from the eye 14, radiation 19 incident on the eye 14 from a source of illumination 20. The illumination source 20 can, in a preferred embodiment, comprise a source of a plurality of wavelength ranges, although this is not intended as a limitation, the use of which will be described in the following.

In use, the software 17 receives images from the cameras 11, 12 and processes the images for display through a stereo microscope 21 that is typically an element of the surgical system, and with the use of which the surgeon is familiar in such procedures. The software 17 can also comprise code segments for superimposing additional data upon the output display, including, but not intended to be limited to, microscope information (zoom, scale factor, measurement bars, etc.) and surgical system information (percent complete of procedure, laser power statistics, etc.). Incorporating such data into the display obviates the need for the surgeon to remove his/her attention from the patient and onto an external display, and these data, as well as any processed image data, can be stored and retrieved for future reference if desired.

Figure 3:
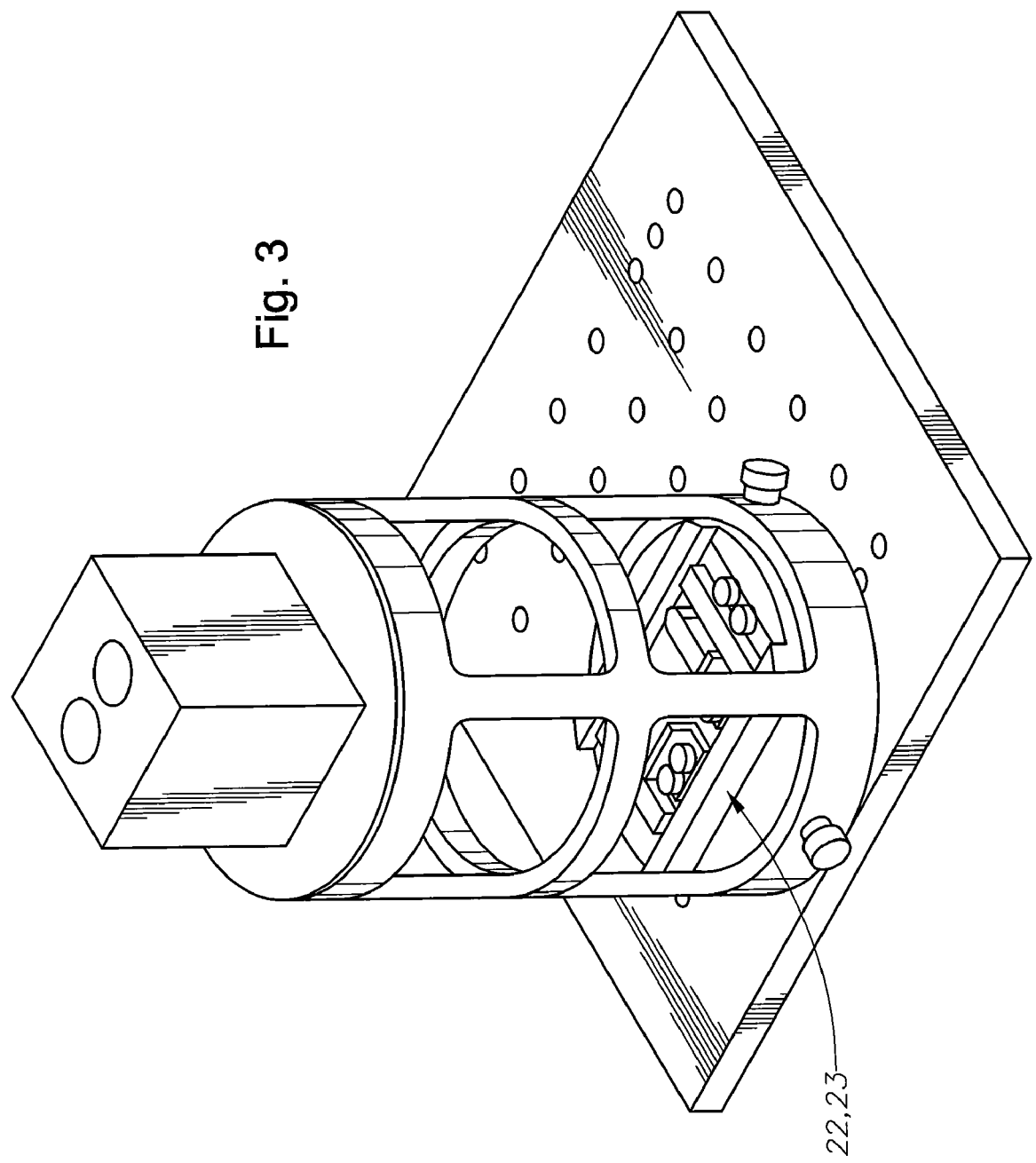
FIG. 3 is a side perspective view of a display assembly.
Figure 5:
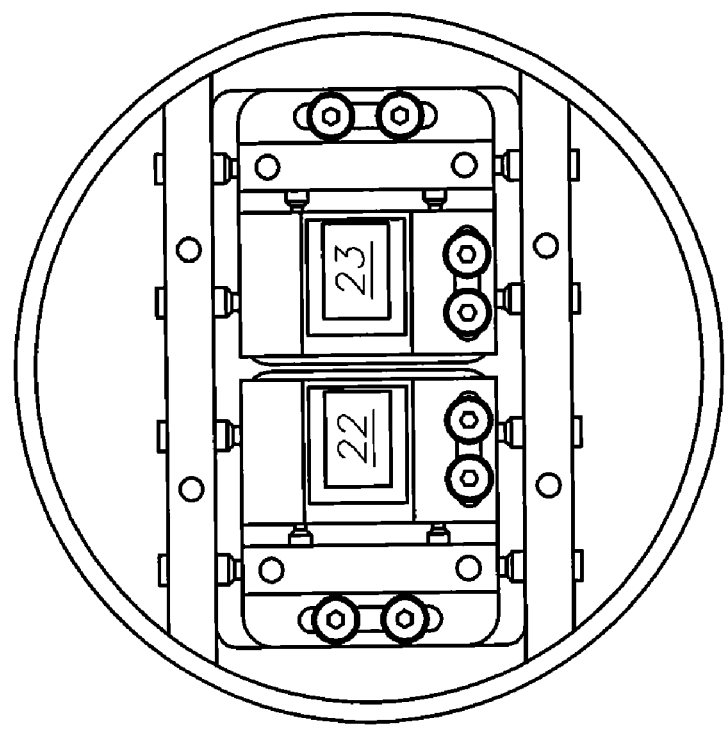
FIG. 5 is a top plan view of the display elements.
Figure 4:
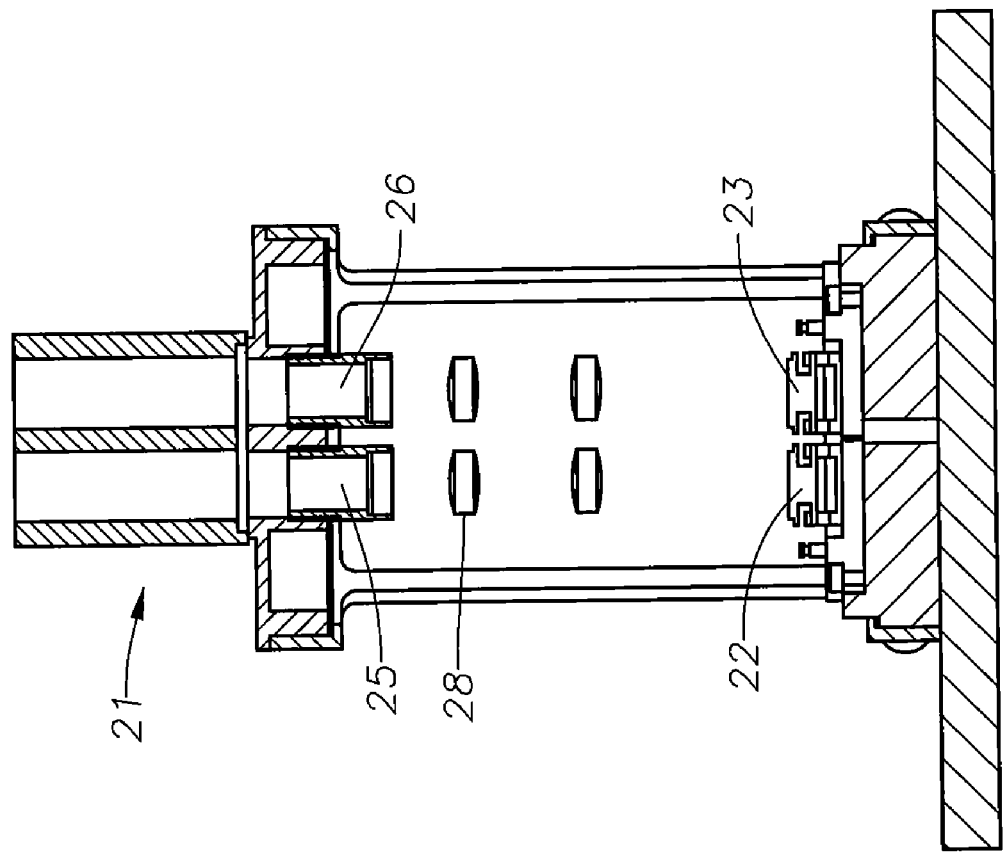
FIG. 4 is a side perspective view of the viewing and display assembly.
Figure 7:
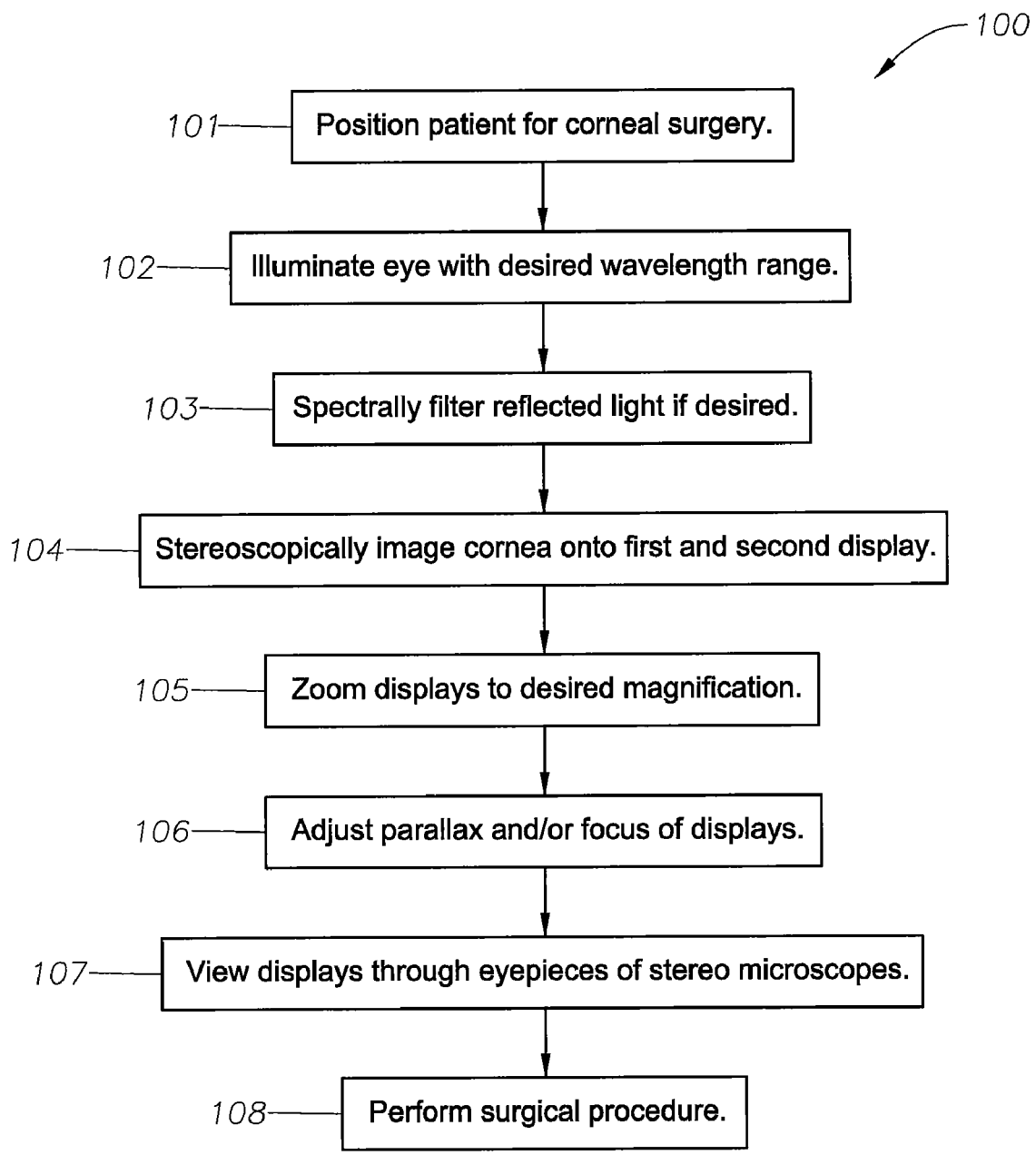
FIG. 7 is a flowchart of an embodiment of the eye imaging and display method of the present invention.

The processed images are transmitted to a first 22 and a second 23 display via display optics 24 for viewing through, respectively, a first 25 and a second 26 eyepiece of the microscope 21 (FIGS. 3-5). The displays 22, 23 can comprise microdisplays for allowing a form factor similar to that of the microscope 21. The displays 22, 23 should preferably have a resolution sufficient so that the surgeon does not see individual pixels thereon. Preferably the displays 22, 23 should have adjustable intensity and contrast. The display optics 24 provide a microscope-like view of the eye 14, having adjustable parallax and focus for each eyepiece 25, 26.

The system 10 can additionally comprise zoom optics 27, which can comprise, for example, true zoom, step-zoom, or true zoom with detents, although these are not intended as limitations. Since the performance of the optics is keyed to the pixel size of the cameras 11, 12 and not retinal resolution, the system design is more flexible, and larger apertures can be used if desired. Preferably the optics should perform over the desired waveband.

The system 10 can further comprise spectral filters 28 that can be interchangeable or switchable, and can be manually switched, placed on a filter wheel, or electrically inserted into the optical pathway. Thus the illumination and the images received by the cameras 11, 12 can be chosen to selectively enhance a desired portion of the eye 14, a feature that is not available when using direct-view microscopes such as known in the art. For example, near-infrared radiation can be used to enhance the pupil, or ultraviolet light can be used to image the corneal surface, which is transparent to visible light but is opaque to ultraviolet light. Non-visible light would appear in black and white on the displays. During a corneal ablation procedure, near-infrared radiation would permit improved visualization of the cornea, and improve patient comfort, since this wavelength range is not visible to the patient. Further, the processor 16 can process the image to enhance the flap and the flap's edge to visualize the stroma. Prior to the flap's being cut, the spectral filters 28 can assist in aligning the patient. Additionally, lower light levels can be used that those that are typically required in direct viewing, since the cameras and processor can be used to adjust gain without flooding the patient's eye with an uncomfortable level of illumination.

In an exemplary embodiment, not intended as a limitation, the surgical monitoring system 10 can be incorporated into a LASIK apparatus for performing corneal ablation (FIG. 6). Two of the aspects of the LASIK apparatus include an optical pathway for the image 30 and for the tracker 31, each of which receives data via beamsplitters 32, 33. Here two illumination sources are illustrated as being directed toward the eye 14, an infrared illuminator 20a and a visible light illuminator 20b.

The zoom lenses 27 can comprise continuous or step-zoom lenses, and optical filters 28 may be included. The cameras 11, 12 comprise high-resolution 2K×2K cameras. A dual frame grabber and video processor 16 display an image onto the two high-resolution (2K×2K) displays 22, 23.

A method 100 (FIG. 7) for monitoring a process of corneal or other eye surgery comprises the steps of positioning the patient for surgery (block 101) and illuminating the patient's eye with a desired wavelength range (block 102). If desired, light reflected from the eye 14 can be spectrally filtered 28 (block 103). The cornea 15 or other eye portion is then imaged stereoscopically onto the first and second displays 22, 23 (block 104), which can be zoomed if desired to a desired magnification (block 105). Parallax and/or focus of the displays 22, 23 can also be adjusted as desired (block 106). The surgeon can view the displays 22, 23 (block 107) through the eyepieces 25, 26 of the surgical microscope 21, prior to, during, and/or following the surgical procedure (block 108).

In the foregoing description, certain terms have been used for brevity, clarity, and understanding, but no unnecessary limitations are to be implied therefrom beyond the requirements of the prior art, because such words are used for description purposes herein and are intended to be broadly construed. Moreover, the embodiments of the system and method illustrated and described herein are by way of example, and the scope of the invention is not limited to the exact details disclosed.

Having now described the invention, the construction, the operation and use of preferred embodiments thereof, and the advantageous new and useful results obtained thereby, the new and useful constructions, and reasonable mechanical equivalents thereof obvious to those skilled in the art, are set forth in the appended claims.

What is claimed is:

1. A system for monitoring a process of corneal surgery comprising:
    a processor;
    a first and a second camera in signal communication with the processor and positionable for focusing on a cornea of an eye positioned for undergoing surgery;
    a first and a second display, and optics therefore, in signal communication with the processor and positionable for viewing through a first and a second eyepiece of a stereo microscope, respectively, the microscope associated with a surgical field of the cornea;
    a source of illumination directable toward the cornea and comprising a wavelength selected for enhancing an image of a portion of the eye; and
    software resident on the processor comprising code segments for:
        receiving a first and a second image of the cornea from the first and the second cameras;
        processing the received first and second images for display; and
        transmitting the processed first and second image to the first and the second displays, respectively, for viewing via the display optics by a surgeon through the microscope at least during the surgery, wherein the first and the second camera each comprise a color camera.

2. The system recited in claim 1, further comprising a spectral filter positionable in front of the camera for transmitting illumination reflected from the eye of a desired frequency range.

3. The system recited in claim 1, wherein the illumination source comprises at least one of a source of near-infrared light and a source of ultraviolet light.

4. The system recited in claim 1, wherein the display optics include means for zooming the display.

5. The system recited in claim 1, wherein the first and the second camera and the first and the second display each have a resolution at least as great as a resolution of a human retina.

6. The system recited in claim 1, wherein the display optics comprise means for adjusting at least one of parallax and focus for each of the first and the second displays.

7. A method for monitoring a process of corneal surgery comprising the steps of:
    illuminating an eye comprising a cornea positioned for undergoing surgery;
    stereoscopically imaging the cornea onto a first and a second display; and
    viewing the first and the second display through a first and a second eyepiece of a stereo microscope, respectively, wherein:
    the imaging step is performed with the use of a first and a second color camera; and
    the illuminating step comprises illuminating the eye with a wavelength selected for enhancing an image of a portion of the eye.

8. The method recited in claim 7, further comprising spectrally filtering illumination reflected from the eye of a desired frequency range upstream of the first and the second camera.

9. The method recited in claim 7, wherein the selected wavelength comprises at least one of near-infrared light and ultraviolet light.

10. The method recited in claim 7, further comprising the step of zooming the display to a desired magnification.

11. The method recited in claim 7, further comprising the step of adjusting at least one of parallax and focus for each of the first and the second displays.

* * * * *